United States Patent
Percher (12)

(10) Patent No.: US 6,785,911 B1
(45) Date of Patent: Sep. 7, 2004

(54) AUTOMATIC ACTUATOR FOR AEROSOL CONTAINERS

(76) Inventor: Marvin J. Percher, 5280 N. Ocean Dr., Apt. 5F, Singer Island, FL (US) 33404

( * ) Notice: Subject to any disclaimer, the term of this patent is extended or adjusted under 35 U.S.C. 154(b) by 0 days.

(21) Appl. No.: 10/713,797

(22) Filed: Nov. 13, 2003

(51) Int. Cl.[7] .................................................. E03D 9/00
(52) U.S. Cl. ........................ 4/228.1; 222/180; 222/649; 222/402.13; 239/274
(58) Field of Search .................... 4/222, 228.1; 222/20, 222/180, 402.13, 402.15, 508, 509, 642, 643, 645, 649; 239/274

(56) References Cited

U.S. PATENT DOCUMENTS

| | | | |
|---|---|---|---|
| 3,023,427 A | 3/1962 | Behringer | |
| 3,309,817 A | 3/1967 | Fisher | |
| 3,318,489 A | 5/1967 | Graves | |
| 3,617,214 A | 11/1971 | Dolac | |
| 3,704,830 A | 12/1972 | Faso | |
| 3,739,944 A | * 6/1973 | Rogerson | .................... 222/649 |
| 3,739,949 A | * 6/1973 | Chimer et al. | .............. 222/180 |
| 3,994,440 A | 11/1976 | Mancini | |
| 4,171,776 A | 10/1979 | Pagliaro | |
| 4,358,860 A | 11/1982 | Church | |
| 5,055,822 A | * 10/1991 | Campbell et al. | ........... 222/644 |
| 5,862,532 A | 1/1999 | Cain | |

* cited by examiner

*Primary Examiner*—Tuan N. Nguyen
(74) *Attorney, Agent, or Firm*—McHale & Slavin, P.A.

(57) ABSTRACT

An automatic dispersing device for dispersing an aerosol from a container having a spring-loaded or pressure biased valve top. The device includes a housing for receiving an aerosol container in an upright position having an opening allowing dispersion of the vapor or aerosol therethrough. An actuation assembly for actuating the valve comprises a rotatable shaft positioned to be proximate the top of the valve, an actuation arm mounted on the rotatable shaft which rotates with respect to the longitudinal axis of the housing, and an eccentric cylindrical cam mounted on the rotational shaft positioned to engage with the valve of the aerosol container. The cam biases the actuation arm outward from the longitudinal axis of the housing at an acute angle in an unactuated state, whereby downward rotation of the actuation arm causes the cam to depress the valve to release a vapor. The spring-loaded valve then returns the actuation arm to its unactuated position.

9 Claims, 6 Drawing Sheets

AUTOMATIC ACTUATOR FOR AEROSOL CONTAINERS

FIELD OF THE INVENTION

This invention is related to the field of aerosol dispensers used for dispersing a quantity of vaporized air freshener, deodorant substance, anti-bacterial agent or the like into a room, and more particularly to an automatic actuator which houses standard aerosol containers which can be wall, door or toilet mounted.

BACKGROUND OF THE INVENTION

Various arrangements exist in the prior art in which the dispersion valve of an aerosol product adapted to be operated in response to a mechanical action, such as a door opening. The aerosol products contain a fluent under pressure for vaporized dispersion and are typically referred to as "air fresheners" which can include perfumes, deodorizers, anti-bacterial agents and the like.

Dolac, U.S. Pat. No. 3,617,214, discloses a door-operated air freshener assembly which has a bracket for support of an aerosol air freshener container. The device is responsive to the opening and/or closing motion of the door and includes a solenoid which is momentarily energized in response to door movement for operation of the nozzle and valve of the container.

Graves, U.S. Pat. No. 3,318,489, discloses a door-operated space conditioning dispenser which includes a replacement hinge pin for the door having a bracket mounted thereon. The bracket includes a depressor mounted on the bracket which activates the dispensing nozzle of the aerosol container.

Pagliaro, U.S. Pat. No. 4,171,776, discloses a door-mounted actuating device for use with a spray container which includes a frame for supporting the container and locating its spray nozzle at door top height, and an actuating mechanism having a pivotally mounted lever arm and a plunger assembly including a plunger rod movable to pivot the lever arm to cause a spray of fluid from the container when the door is opened and closed.

Heropoulos, U.S. Pat. No. 3,309,817, discloses an aerosol holder with a door actuated valve actuator. Each time a door is swung open, it engages a resilient actuating means similar to a doorstop which moves a plunger inwardly through a passage to depress the plunger of a sideways mounted aerosol container.

Faso, U.S. Pat. No. 3,704,830, discloses a door-mounted spraying device for an aerosol container which includes a metal clip to fit over the door so that no tools or fastening means are needed for installation.

Mancini, U.S. Pat. No. 3,994,440, discloses a spray unit attachable to a door which ejects a spray into a room when the attached door is in the open position. A bracket holds an aerosol can in an upright position, and a spring-biased knob which may be pushed downwards is pivotally mounted in the bracket directly over the center push button of the attached aerosol can. A wire rod which passes through the bracket is pivotally mounted to the door jam.

Behringer, U.S. Pat. No. 3,023,427, discloses a device for sterilizing and deodorizing toilet bowls. A bracket is used to attach an aerosol can inside the tank. When an actuating lever is pivoted, the aerosol can is discharged through a conduit into the toilet discharge tank.

Church, U.S. Pat. No. 4,358,860, discloses an automatic actuator for dispensers for air fresheners and the like from an aerosol container mounted on the interior of a toilet tank. An actuator arm has one end connected to the neck of the container, and a flexible tube extends from the outlet of the container to the exterior of the toilet tank. A pull rod is pivotally attached to the actuator arm, and has a cup suspended thereon which rises and falls with the water level of the tank, causing the actuator to dispense the air freshener.

Cain, U.S. Pat. No. 5,862,532, discloses a dispenser mounted on the exterior of a toilet bowl having a housing containing an aerosol spray can installed with the nozzle pointed downward. A length of tubing directs the spray into the toilet bowl.

A disadvantage of the above-described prior art devices intended for use with aerosol containers is that they have numerous moving parts, and are relatively complex in operation, and are limited to a single dispensing use. Moreover, many are intended for only one type of aerosol canister configuration, i.e. a depressable valve member mounted on an extended stem. Many of the current aerosol containers presently marketed have an ergonomic, flush mounted valve actuation means, and would not be suitable for use with the prior art devices.

Thus, it would be highly advantageous to provide an automatic actuator for aerosol containers which can be readily adapted to a variety of aerosol dispensing canister sizes and shapes, can be used numerous applications, and which has a minimum number of moving parts.

SUMMARY OF THE INVENTION

It is an objective of the invention to provide an automatic actuator for aerosol containers which can be installed to function as either a door-actuated or toilet lever-actuated device.

It is another objective to provide an automatic actuator for aerosol containers which has a minimal number of mechanical parts.

It is still another objective to provide an automatic actuator for aerosol containers which utilizes an eccentric cylindrical cam to actuate the aerosol container, and thus allows the device to be used with aerosol containers of diverse size, shape, or dispenser orientation.

It is a further objective of the invention to provide an automatic actuator for aerosol containers which can be inexpensively manufactured.

It is yet a further objective of the invention to provide an automatic actuator for aerosol containers which can be mounted on either the door or a wall surface adjacent the door in order to actuate the aerosol container when the swinging door is proximate the wall surface.

It is still a further objective of the invention to provide an automatic actuator for aerosol containers which can be mounted in a hanging arrangement on a toilet tank adjacent the flush lever, so that depression of the flush lever actuates the aerosol container.

It is still another objective to provide an automatic actuator for aerosol containers which functions "on demand" allowing for an extended life for the canister contents.

It is still another objective to provide an automatic actuator for aerosol containers which utilizes standard "off the shelf" aerosol canisters.

It is still another objective to provide an automatic actuator for aerosol containers which is mechanical in operation and does not require an external power source.

It is still another objective of the invention to provide an automatic actuator for aerosol containers which can be used in combination with various sizes of containers.

In accordance with the above objectives, a device for dispersing a vapor from a standard "off the shelf" aerosol container having a spring-loaded valve top is provided. In a preferred embodiment adapted for aerosol containers having a vertical spray trajectory, the device includes a housing for receiving the aerosol container in an upright position. The housing has a vertically oriented longitudinal axis and a generally open top allowing dispersion of the vapor therethrough. The housing is defined by a bottom wall, left and right opposing side walls, a back wall and a front wall. At least one of the walls is displaceable to provide an opening for the insertion of the aerosol container therein. In a preferred embodiment, the front wall is removable. In an alternative embodiment, the housing can be adapted to receive aerosol containers which have a forward spray trajectory. In this embodiment, the front wall is configured to allow forward dispersion through the front of the housing.

The device includes an actuation assembly for actuating the valve of the aerosol container which includes a rotatable shaft extending orthogonally from at least one of the opposing side walls and positioned to be proximate the top of the spring-loaded valve of an aerosol container inserted in the housing. An actuation arm mounted on the rotatable shaft which rotates with respect to the longitudinal axis of the housing, and an eccentric cylindrical cam is mounted on the rotational shaft and is positioned to engage with the spring-loaded valve of the aerosol container. The eccentric cam biases the actuation arm outward from the longitudinal axis of the housing at an acute angle in an unactuated state, whereby downward rotation of the actuation arm causes the cam to depress the aerosol container valve to release a vapor. The spring-loaded valve then returns the actuation arm to its unactuated position.

The actuation arm is adapted to engage with a laterally approaching vertical planar surface, such as a swinging door, whereby said actuation arm is rotated downward by the planar surface. The back wall can include mounting apertures adapted to receive fasteners therethrough whereby said housing can be mounted on a planar surface. The device can be mounted on a hingedly-mounted door on the surface of the door inside the swinging arc so that the actuation arm is rotated when the door swings to a point proximate a wall surface adjacent to the door and the actuation arm contacts the wall. In another arrangement, the device can be mounted on a wall surface inside the swinging arc of a hingedly mounted door, and the actuation arm is rotated when the door swings toward the wall surface and contacts the actuation arm.

In an embodiment adapted for installation to a toilet tank, the actuation arm terminates in at least one lateral extension, preferably in a L-shaped configuration. The housing further includes a means to attach the device to the exterior of a toilet tank in a hanging arrangement so that the housing is positioned on the toilet tank proximate the flush lever so that the lateral extension is positioned below the flush lever. The lateral extension of the actuation arm is then depressed each time the flush lever is engaged and a quantity of air freshener is dispersed from the aerosol container.

In order to attach the housing to the exterior of a toilet tank a bracket is provided which is attachable to the back wall of the housing. The bracket has first and second planar surfaces orthogonal to one another. The first surface includes slotted apertures coincident with the mounting apertures in the back wall which allow the first planar surface to be fastened to the back wall. The second planar surface terminates in a hook member adapted for hanging engagement with the edge of the open toilet tank.

DETAILED DESCRIPTION OF THE INVENTION

Although the invention will be described in terms of a specific embodiment, it will be readily apparent to those skilled in this art that various modifications, rearrangements, and substitutions can be made without departing from the spirit of the invention. The scope of the invention is defined by the claims appended hereto.

Figure 1:
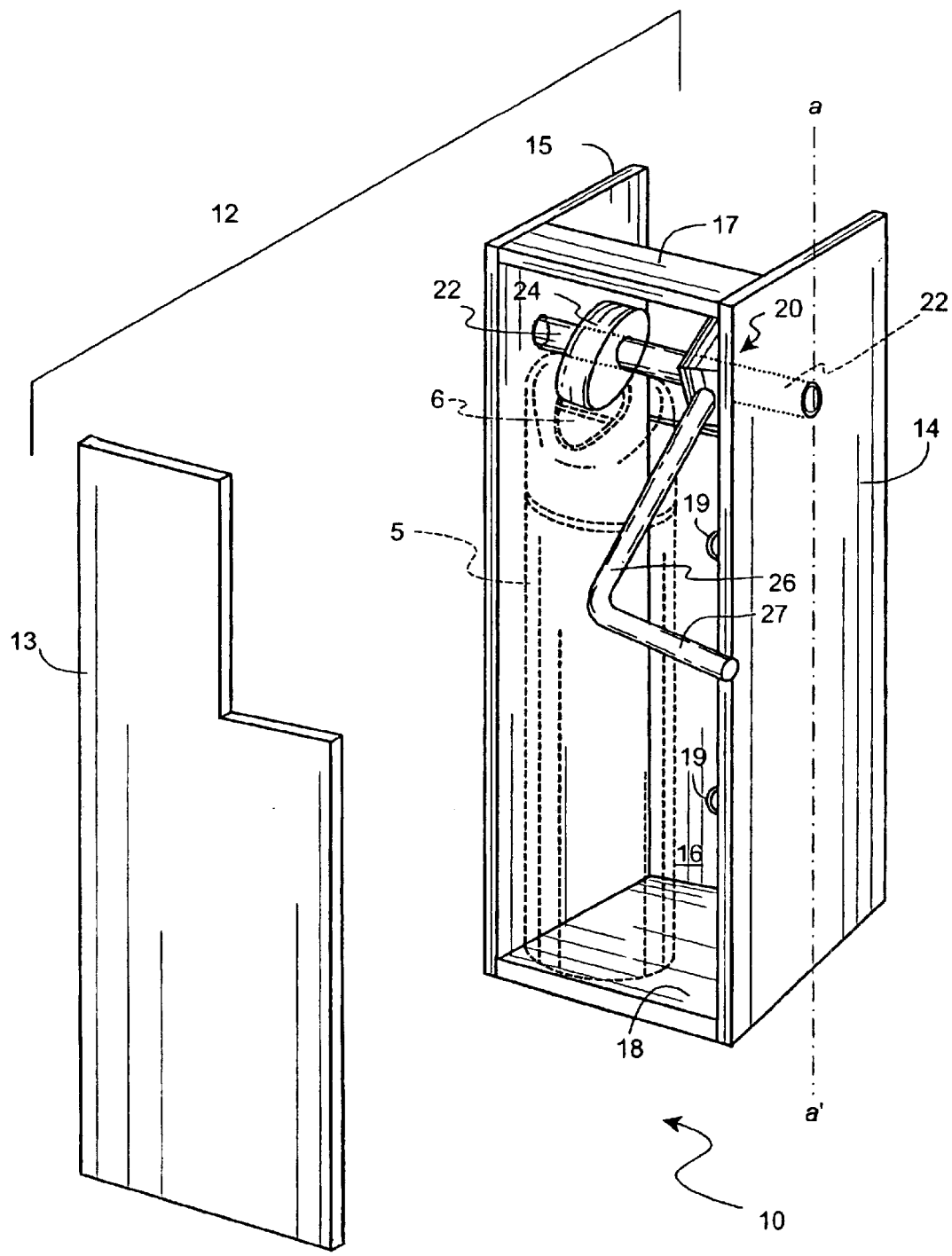
FIG. 1 is a perspective view of the automatic actuator for aerosol containers according to a preferred embodiment of the invention with the front wall detached and an aerosol container shown therein in phantom.

FIG. 1 illustrates an automatic actuator for aerosol containers according to a preferred embodiment of the invention. The device 10 is used in combination with a conventional cylindrical aerosol container 5 having a spring-loaded or pressure biased valve top 6 as is commonly commercially available. In the practice of the invention, the aerosol container 5 is an "air freshener" and contains a deodorant, fragrance, anti-bacterial agent or the like under pressure which disperses as a vapor/aerosol from the valve top 6 when the valve top 6 is depressed toward the body of the container. It is an advantage of the present invention that the device 10 is used with "off the shelf" aerosol containers sold at the retail level, and does not require aerosol canisters having a specialized configuration.

The device 10 includes a housing 12 for receiving the aerosol container 5, and has a generally open top which allows dispersion of the vapor therethrough. The housing 12 is defined by a plurality of walls including a front wall 13, left and right side walls 14 and 15, a back wall 16, and a bottom wall 18, where at least one of the walls is displaceable to provide an opening for insertion of the aerosol container 5.

In the preferred embodiment, the front wall 13 is removable, and in FIG. 1 is shown detached from the housing 12 for ease of illustration. The back wall 16 includes mounting apertures 19 which are adapted to receive fasteners, such as screws (not shown), which allow the device 10 to be mounted upon a planar surface, such as a wall or door. For stability, a top support panel 17 can extend between the opposing side walls 14, 15.

The embodiment shown in FIG. 1 is adapted for use with containers having a vertical spray trajectory, and thus includes a top opening. In alternative embodiments, the housing can be configured to accommodate containers having a lateral spray trajectory. In this embodiment, the front wall is configured to allow forward dispersion therethrough.

Figure 3:
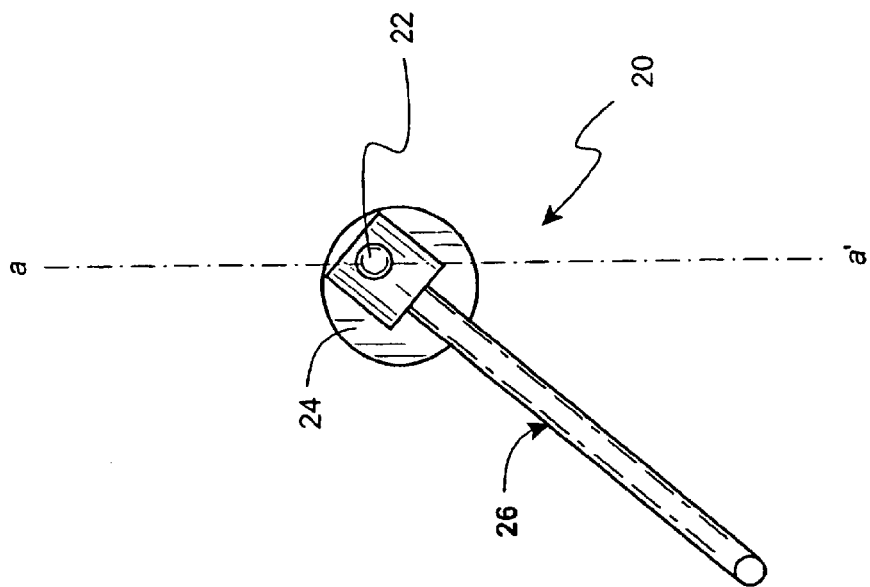
FIG. 3 is a side view of the actuation assembly of the device shown in FIG. 1.
Figure 2:
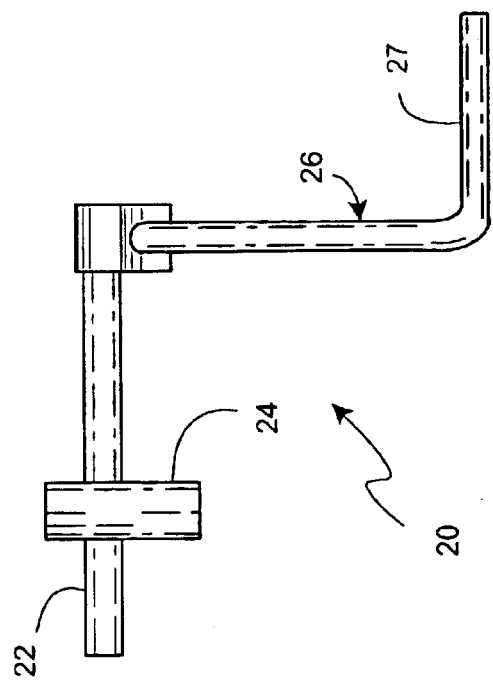
FIG. 2 is a front view of the actuation assembly of the device shown in FIG. 1.

The device 10 includes an actuation assembly 20 for actuating the valve top 6 of the aerosol container 5, which is illustrated in detail in FIGS. 2 and 3. The actuation assembly 20 includes a rotatable shaft 22 which extends orthogonally from at least one of the opposing side walls 14, 15, and is positioned in the housing to be directly above the aerosol container 5 when such is inserted into the housing. In the preferred embodiment, the rotatable shaft 22 extends between the opposing side walls 14, 15. An actuation arm 26 is mounted on the rotatable shaft 22 so that the actuation arm 26 rotates with respect to the longitudinal axis α–α' of the housing. In FIG. 1, the actuation arm 26 is positioned within the housing 12, however the actuation arm 26 can also be mounted on the rotatable shaft 22 so as to be outside of the housing. The actuation arm 26 can include at least one lateral extension 27. In the preferred embodiment, the lateral extension 27 provides a substantially L-shaped configuration.

Figure 4:
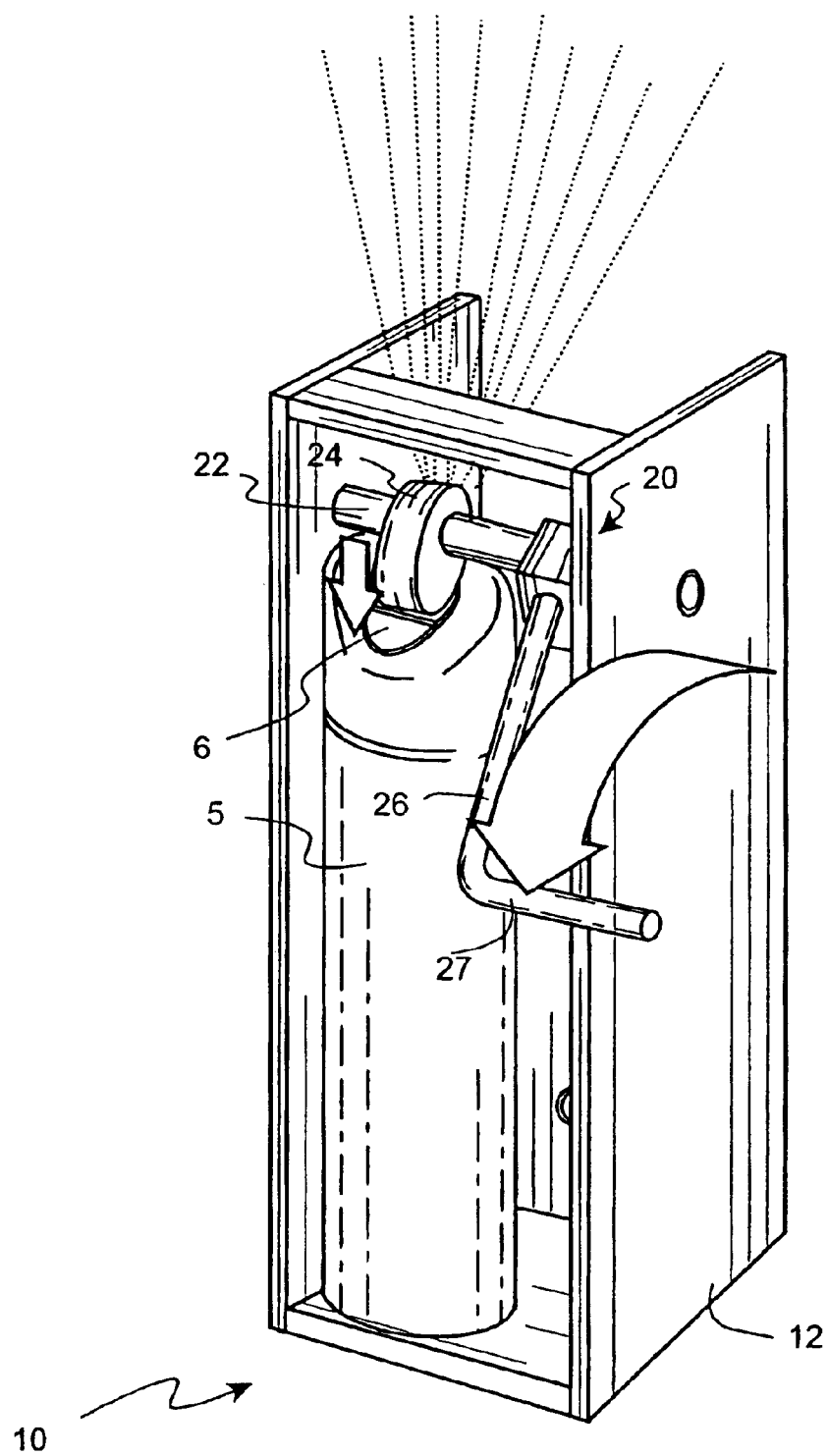
FIG. 4 is a perspective view of the device shown in FIG. 1 in which the actuation arm has been rotated to actuate the aerosol container valve.

An eccentric cam 24 is mounted on the rotational shaft 22 and positioned to engage with the valve 6 of an aerosol container 5 inserted in the housing. The eccentric cam 24 can have any suitable configuration, and is preferably an eccentrically mounted cylindrical member. The fixed position of the actuation arm 26 with respect to the eccentric cam 24 is such that the actuation arm 26 extends from the longitudinal axis α–α' at an acute angle when the eccentric cam 24 is in an unactuated position. When the actuation arm 26 is rotated downwardly, as shown in FIG. 4, the eccentric cam 24 depresses the valve 6 and a quantity of vapor is dispersed. When the actuation arm 26 is released, the spring-loading of the valve 6 serves to return the actuation arm 26 to its original unactuated position. In the practice of the invention, the relative angular position of the eccentric cam 24 and the actuation arm 26 can be adjusted to achieve varying durations of vapor spray.

Figure 5:
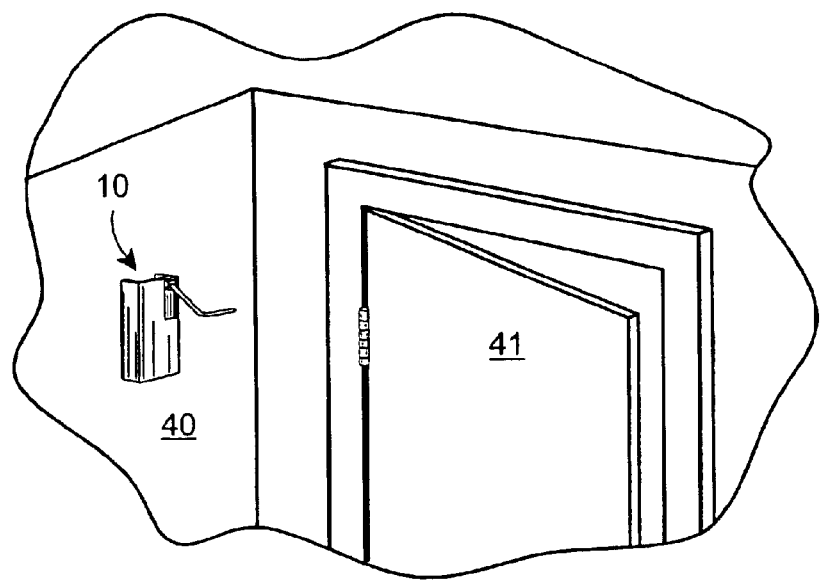
FIG. 5 illustrates an installation arrangement in which the device of the invention is mounted on a wall proximate a hingedly-mounted swinging door.

The angled position of the actuation arm 26 in its unactuated position advantageously allows the actuation arm 26 to engage with a laterally approaching vertical planar surface. In FIG. 5, the device 10 is shown mounted on a wall 40 proximate a hingedly-mounted swinging door 41. The device 10 is positioned on the wall 40 inside the arc defined by the swinging of the door 41 so that the device 10 contacts the door 41 when the door 41 is swung to a fully open position. Thus, when the fully open door depresses the actuation arm 26 to an actuation point, a quantity of vapor is released into the room.

Figure 6:
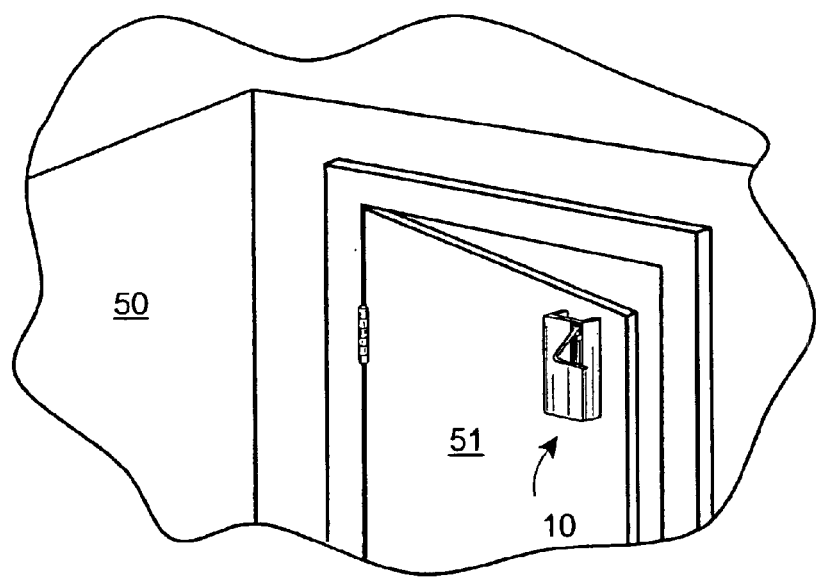
FIG. 6 illustrates an installation arrangement in which the device of the invention is mounted on a door inside its swinging arc.

In a similar arrangement shown in FIG. 6, the device 10 is mounted on the door 51 on the surface of the door 51 inside its swinging arc. When the door swings to a point proximate a wall surface 50 adjacent to the door 51, the actuation arm 16 is rotated when the actuation arm 26 contacts the wall surface 50. With a continued opening motion of the door 51, the actuation point is reached and the valve of the aerosol container is actuated.

In either of the arrangements shown in FIGS. 5 and 6, activation of the aerosol container can be essentially passive on the part of the user, where release of the vapor occurs only when the door is opened to the actuation point. If desired, the user can actively initiate the release of the vapor by opening the door to the actuation point. The user can also hold the door at the actuation point until the desired quantity of vaporized product is released. The device of the present invention can be installed anywhere it is desired to emit a vaporized air freshener product. The device 10 can be used, for example, in public restroom stalls so that a deodorizing product is passively released each time someone enters the stall, or when the device is deliberately activated by holding the swinging door at the actuation point. The invention advantageously allows manual dispersion of the vapor on an "on demand" basis, as opposed to timer-actuated automatic dispersion, and therefore can extend the life of the aerosol contents.

Figure 7A:
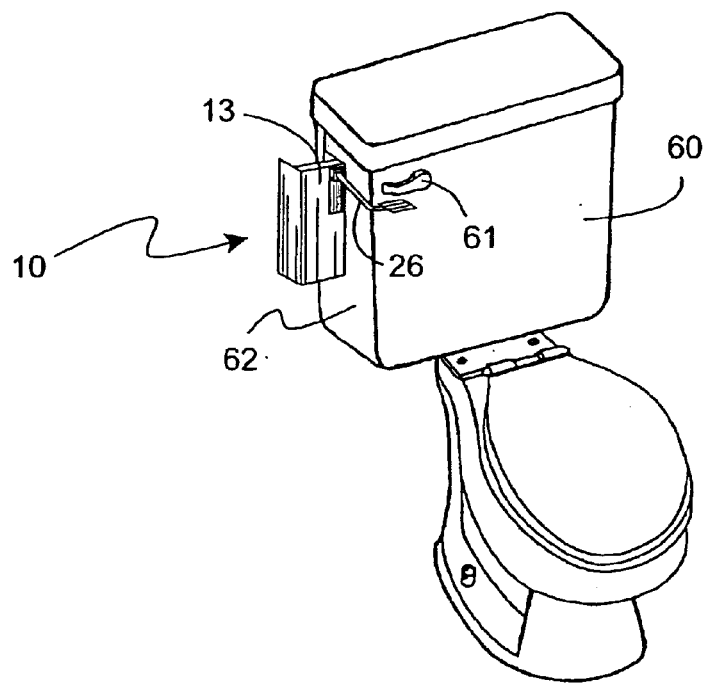
FIG. 7A illustrates an alternative arrangement of the device of the invention in which the device is attached to a toilet tank.
Figure 7B:
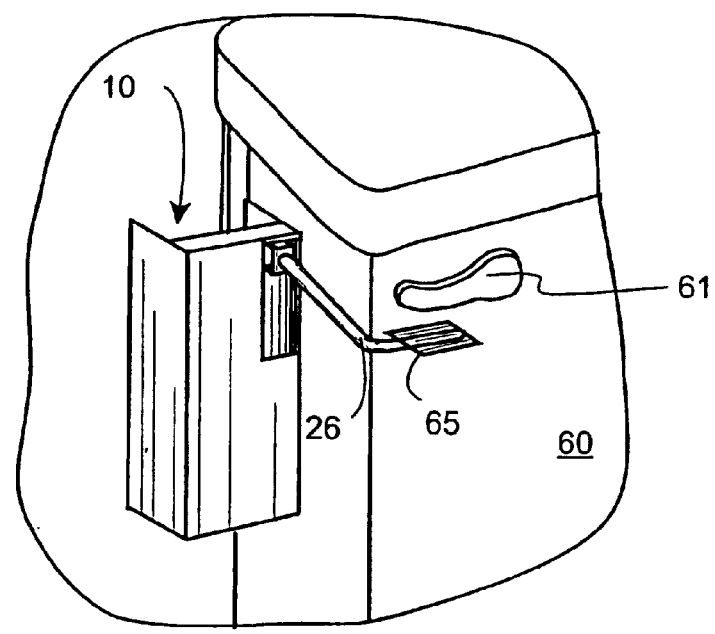
FIG. 7B is a detail view of the arrangement shown in FIG. 7A.

FIGS. 7A and 7B illustrate an alternative arrangement of the device 10 in which the device 10 is attached to a toilet tank 60. In this arrangement, the actuation arm 26 is rotated by the manual action of pressing flush lever 61 of the toilet tank 60. As shown in the illustrations, the device 10 is attached to the right lateral side 62 of the toilet tank 60 proximate the flush lever 61. (The illustrated arrangement is applicable to a right-hand oriented toilet tank, however it will be readily appreciated that the invention could be used in a left-handed arrangement in the opposite configuration.)

The front wall 13 faces forward with respect to the toilet tank 60 so that the left opposing side wall 15 (not visible in the illustration) is adjacent to the right lateral side 62 of the toilet tank 60. The device 10 is positioned so that the lateral extension 27 is in the line of intersection with the path of the flush lever 61. In this arrangement, the actuation arm 26 can have any suitable configuration which permits engagement with the flush lever 61. In the illustrated embodiment, the actuation arm 26 includes planar extension 65 in order to provide a larger contact area. The downward motion of the flush lever 61 thus serves to actuate the valve of the aerosol container to disperse an air freshening composition each time the flush lever 61 is actuated.

Figure 8:
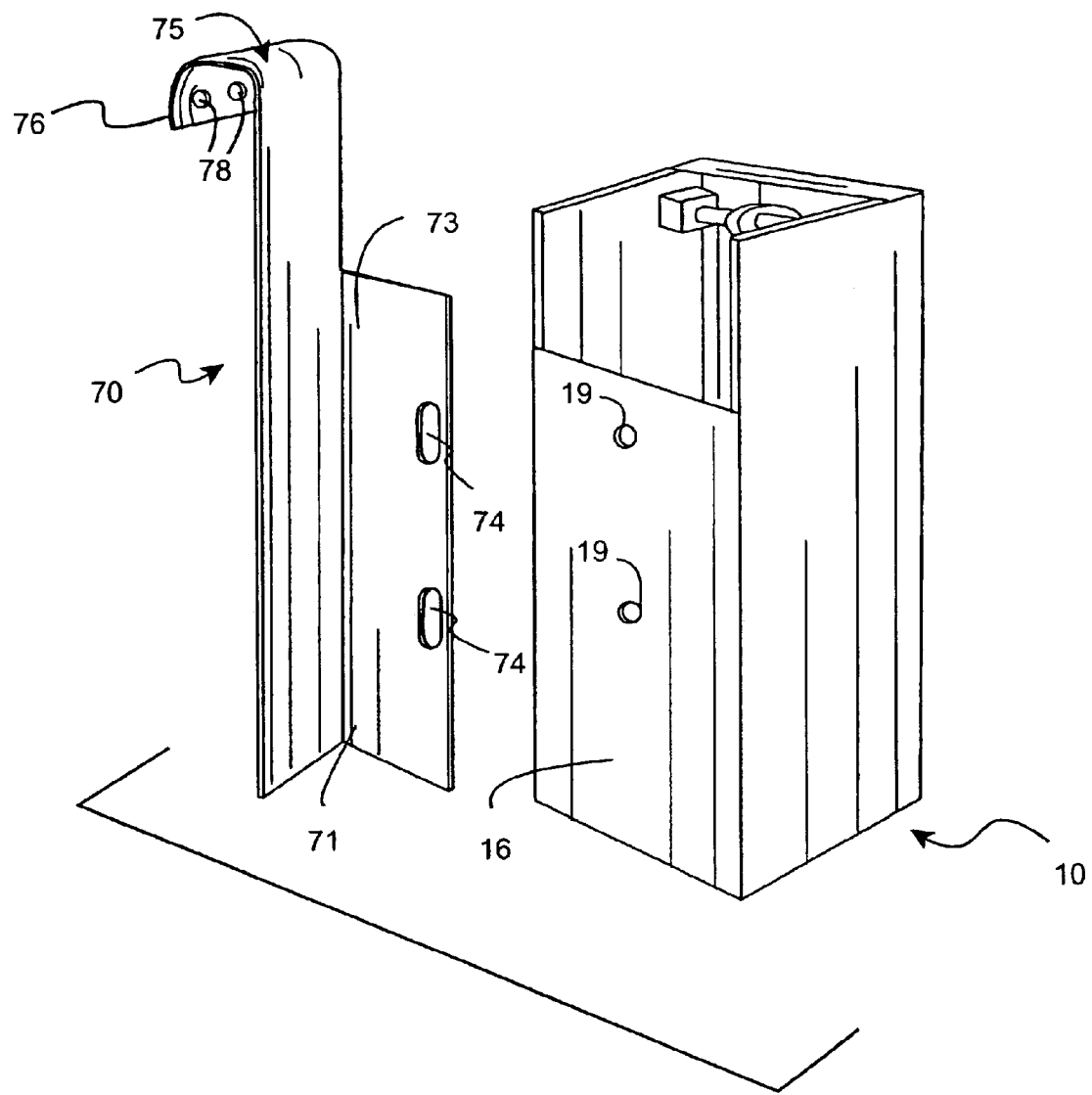
FIG. 8 illustrates a hanging bracket attachable to the device of the invention.

The invention contemplates any number of arrangements by which the device 10 can be attached to the toilet tank 60. In the preferred embodiment, the device 10 is attached to the toilet tank 60 in a hanging arrangement, wherein the cover 63 is removed to allow attachment of the device 10 and then replaced. The device 10 can be attached to a hanging bracket 70, as shown in FIG. 8. The hanging bracket 70 can have any suitable configuration, and the invention is not limited to the illustrated arrangement. The hanging bracket 70 includes first and second planar surfaces 71, 73 in an orthogonal arrangement. The first planar surface includes vertically oriented slotted apertures 74 which align with the mounting apertures 19 in the back wall 16 of the housing 12. The first planar surface 71 can be secured to the back wall 16 by insertion of fastening members therethrough. The upper end 75 of second planar surface 73 is formed as a hook 76 adapted for hanging engage on the edge of the toilet tank 60. The bracket 70 can include a means to secure the bracket 70 to the toilet tank 60. In a preferred embodiment, the hook 76 includes a plurality of apertures 78 adapted to receive threaded screws (not shown) which engage with the external surface of the toilet tank 60.

In order to attach the device 10 having the hanging bracket 70 attached thereto to the toilet tank 60, the cover of the tank 60 is removed, and the hook 76 is engaged with the lip of the toilet tank 60 so that the device 10 is suspended proximate the flush lever 61. In the practice of the invention, the position of the device 10 is adjusted at the time of installation to ensure that the device 10 is in the optimal position for engagement with the flush lever 61. To this end, the vertically oriented slotted apertures 74 advantageously allow vertical adjustment of the housing 12 with respect the toilet tank 60. At the same time, horizontal adjustment can be accomplished by varying the location of the hook 76 on the lip of the toilet tank 60. In this way, the bracket 70 permits universal adjustment of the position of the device 10 with respect to the toilet tank 60 so that optimal operation is achieved.

An advantage of the present invention is that the device 10 can be used in combination with various sizes and shapes of "off the shelf" aerosol containers. It has been found by the present invention that the cylindrical configuration of the eccentric cam can advantageously engage with any type of spring loaded or pressure-biased valve on an aerosol container. For example, the eccentric cam is operable to depress a standard type aerosol valve mounted on an extended stem as well as the flush-mounted ergonomic type valves commonly used for air freshener products. To accommodate containers of different heights, the housing 12 can include spacer members insertable underneath the aerosol container. The top of the housing 12 and front wall 13 can be configured to accommodate containers of varying spray trajectories. To maintain the aerosol container in alignment within the housing 12, the housing 12 can include various partition members therein. A portion of flexible material, such as rubberized hair, foam rubbers or the like, can also be included in the housing 12 to hold the aerosol container in alignment.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What I claim is:

1. A device for dispensing a vapor or aerosol from an aerosol container having a spring-loaded or pressure-biased valve, comprising:

a housing for receiving an aerosol container in an upright position wherein said housing has a vertically oriented longitudinal axis and has a generally open top for dispersion of said vapor or aerosol therethrough, said housing defined by a plurality of walls including a bottom wall, left and right opposing side walls, a back wall and a front wall wherein at least one of said walls is displaceable to provide access to said housing for insertion or removal of said aerosol container;

an actuation assembly for actuating the valve of the aerosol container, said actuation assembly comprising:

a rotatable shaft extending orthogonally from at least one of said opposing side walls and positioned to be proximate a topmost portion of the valve of an aerosol container inserted in said housing;

an actuation arm mounted on said rotatable shaft wherein said actuation arm rotates with respect to said longitudinal axis of said housing;

an eccentric cam mounted on said rotatable shaft positioned to engage with the valve of an aerosol container inserted in said housing, said eccentric cam effective to bias said actuation arm outward from said longitudinal axis of said housing at an acute angle in an unactuated state, whereby downward rotation of said actuation arm causes said cam to depress said aerosol container valve to release a vapor or aerosol therefrom, and whereby the spring-loaded or pressure biased valve then returns the actuation arm to its unactuated position.

2. The device of claim 1, wherein said actuation arm is adapted to engage with a laterally approaching vertical planar surface, whereby said actuation arm is rotated downward by the planar surface.

3. The device of claim 1, wherein said back wall includes mounting apertures adapted to receive fasteners therethrough whereby said housing can be mounted on a planar surface.

4. The device of claim 3, wherein said device is mounted on a hingedly-mounted door on a surface of said door inside its swinging arc, and said actuation arm is rotated when the door swings to a point proximate a wall surface adjacent to the door and said actuation arm contacts said wall.

5. The device of claim 3, wherein said device is mounted on a wall surface within a swinging arc of a hingedly mounted door, and said actuation arm is rotated when the door swings toward the wall surface and contacts the actuation arm.

6. The device of claim 1, wherein said eccentric cam is cylindrical.

7. The device of claim 1, wherein said front wall is removable.

8. The device of claim 1, wherein said actuation arm terminates in at least one lateral extension, and said housing further includes a means to attach said device to an exterior portion of a toilet tank in a hanging arrangement, whereby said housing is positioned on the toilet tank proximate a flush lever so that said lateral extension is positioned below the flush lever such that the lateral extension is depressed when the flush lever is engaged.

9. The device of claim 8, wherein said means to attach said housing to the exterior portion of a toilet tank comprises a bracket attachable to said back wall of said housing, said bracket having first and second planar surfaces orthogonal to one another, wherein said first surface includes mounting apertures coincident with mounting apertures in said back wall wherein said apertures are adapted to received fasteners therethrough to attach said first planar surface to said back wall, and said second planar surface terminates in a hook member adapted for hanging engagement with an edge of said toilet tank.

* * * * *